United States Patent [19]
Saito et al.

[11] Patent Number: 5,422,075
[45] Date of Patent: Jun. 6, 1995

[54] CHEMICAL LUMINESCENCE-DETECTING APPARATUS WITH MULTIPLE SENSORS

[75] Inventors: Yukio Saito, Yokohama; Koichi Sekiya, Ciba; Yoshihiro Sato, Yokohama; Takeshi Kohno, Hirakata; Hiroaki Takahasi, Kyoto; Kunio Terada, Ohtsu; Takayuki Aoki, Shiga, all of Japan

[73] Assignees: Sankyo Company, Limited, Tokyo; Horiba, Ltd., Kyoto, both of Japan

[21] Appl. No.: 83,401

[22] Filed: May 27, 1993

Related U.S. Application Data

[63] Continuation of Ser. No. 668,779, Mar. 13, 1991, abandoned.

Foreign Application Priority Data

Mar. 13, 1990 [JP] Japan .................................. 2-62190

[51] Int. Cl.$^6$ .................... G01N 21/76; G01N 21/01
[52] U.S. Cl. .................... 422/52; 250/361 C; 250/361 R; 356/224; 422/63; 422/65; 422/67; 436/172
[58] Field of Search .................... 250/361 C, 361 R; 356/224; 422/52, 63, 65, 67, 68.1; 436/172

[56] References Cited

U.S. PATENT DOCUMENTS

| | | | |
|---|---|---|---|
| 3,679,312 | 7/1972 | Mansberg | 250/361 C X |
| 3,690,832 | 9/1972 | Plakas | 422/52 X |
| 3,726,599 | 4/1973 | Neavy | 422/52 X |
| 3,825,762 | 7/1974 | White | 356/51 X |
| 4,052,161 | 10/1977 | Atwood et al. | 422/82 X |
| 4,366,118 | 12/1982 | Bunce et al. | 422/67 X |
| 4,499,052 | 2/1985 | Fulwyler | 422/52 |
| 4,563,331 | 1/1986 | Losee et al. | 422/52 |
| 4,652,735 | 3/1987 | Ishikawa et al. | 356/224 X |
| 4,755,055 | 7/1988 | Johnson et al. | 422/52 X |
| 4,772,453 | 9/1988 | Lisenbee | 422/52 |
| 4,810,658 | 3/1989 | Shanks et al. | 436/172 |
| 4,818,883 | 4/1989 | Anderson et al. | 250/361 C |
| 4,838,689 | 6/1989 | Neumann | 356/73.1 |
| 4,863,690 | 9/1989 | Berthold et al. | 422/52 |
| 5,102,623 | 4/1992 | Yamamoto et al. | 422/65 X |
| 5,122,342 | 6/1992 | McCulloch et al. | 422/65 |
| 5,223,218 | 6/1993 | Fukuoka et al. | 422/52 |

FOREIGN PATENT DOCUMENTS

| | | |
|---|---|---|
| 0355738 | 2/1990 | European Pat. Off. .... 250/361 C |
| 63-73137 | 4/1988 | Japan . |
| 61265552 | 11/1988 | Japan . |
| 64-18186 | 1/1989 | Japan . |
| 2236453 | 9/1990 | Japan . |

OTHER PUBLICATIONS

H. Rasmussen et al. *Chem. Abstr.* 1969, 70, 9303d.
G. W. Mitchell et al. *Chem. Abstr.* 1971, 74, 50356u.
A. Zweig et al. *J. Am. Chem. Soc.* 1968, 90, 261–268.
R. Bezman et al., *Anal. Chem.* 1971, 43, 1749–1753.
H. R. Schroeder et al. *Anal. Biochem.* 1976, 72, 283–292.

Primary Examiner—James C. Housel
Assistant Examiner—Arlen Soderquist
Attorney, Agent, or Firm—Price, Gess & Ubell

[57] ABSTRACT

The present invention relates to a chemical luminescence-detecting apparatus that is provided with a plurality of optical detectors different in sensitivity in the vicinity of a photometric cell. A ratio of outputs from the optical detectors based on intensity of luminescence is previously determined and stored. Signal processing can multiply an output of a low sensitivity optical detector by a factor determined by the stored ratio to measure the intensity of luminescence so that a conversion value corresponding to an equivalent output from a high sensitivity optical detector may be obtained when the output from the high sensitivity optical detector has become saturated.

7 Claims, 7 Drawing Sheets

CHEMICAL LUMINESCENCE-DETECTING APPARATUS WITH MULTIPLE SENSORS

This is a continuation of application Ser. No. 07/668,779, filed Mar. 13, 1991, now abandoned.

BACKGROUND OF THE INVENTION

1. Field of the Invention

The present invention relates to a chemical luminescence-detecting apparatus in which an intensity of a chemical luminescence generated in a photometric cell is detected by an optical detector and, more particularly, to the use of multiple optical detectors with predetermined cooperative characteristics.

2. Description of Related Art

The measurement of the luminescence produced, for example, in a chemical reaction, has been successfully utilized. For example, an enzyme immuno assay system capable of measuring various substances found in blood, such as carcino embryonic antigen (CEA), ferritin (FER), α-fetoprotein (AFP), and thyroxine binding globulin (TBG) is known. Generally, a sample to be measured is put into a container such as a tube that may have a predetermined antibody substance in the tube in order to permit a reaction to be carried out. A substrate solution can be added to carry out an enzyme reaction, thereby generating a reaction liquid containing, for example, hydrogen peroxide. A portion of the resulting reaction liquid containing the hydrogen peroxide can then be placed into the photometric sample cell or tube, together with a luminescent reagent, to measure the substances contained within the tube by detecting the intensity of a chemical luminescence generated in the photometric cell.

Figure 11:
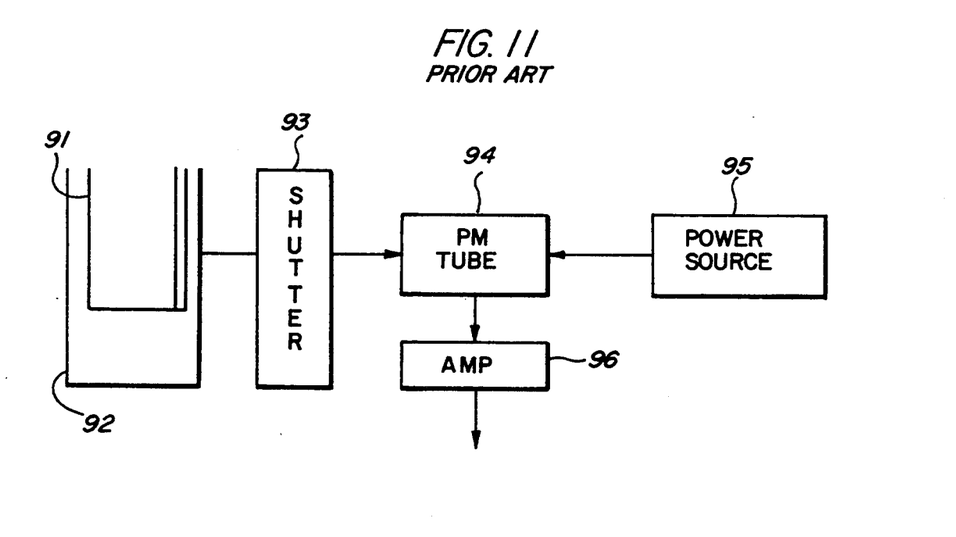
FIG. 11 is a schematic block diagram of a prior art luminescence-detecting apparatus.

Referring to FIG. 11, the schematic of a prior art chemical luminescence-detecting apparatus is disclosed. This apparatus can comprise a cylindrical photometric cell or tube 91 made of glass or plastic, which can be fixedly mounted on an integrated spherical cell holder 92. A shutter mechanism 93 can control light emitting from the photometric cell 91. Adjacent the shutter mechanism 93 is a photomultiplier tube 94 that can receive and detect the chemical luminescence being generated by the reaction within the test cell 91. This apparatus would be useful in a so-called batch-type measuring system, and a high voltage power source 95 can be connected to the photomultiplier tube 94. The output from the photomultiplier tube 94 can be appropriately amplified by an amplifier 96 prior to subsequent signal processing.

According to the conventional luminescence-detecting apparatus shown in FIG. 11, only one photomultiplier tube 94 is provided for measuring the output of the photometric cell 91. In order to enable an increased range of measurement by the photomultiplier tube 94 under similar conditions, it has been frequently necessary to carry out the measurement while regulating other parameters of the system, for example, by varying the supply voltage from the high voltage power source 95, by varying the value of any feedback resistance in the amplifier circuit and the like.

A problem has existed in that the conventional chemical luminescence apparatus can be limited in its ability to accommodate a wide range of measurements. For example, in the enzyme immune measurement systems it has been difficult to use a conventional chemical luminescence-detecting apparatus, since a large number of items must be randomly measured during the enzyme immune measurement system, so that a corresponding large range of quantities of light to be measured can occur. It becomes further difficult to modify the system so that measurements can be carried out by means of only a single optical detector. These problems exist not only in the batch-type measuring method, but also in the so-called flow through-type measuring method that can, for example, use a spiral flow through-type photometric cell.

The prior art is still seeking to optimize chemical luminescence-detecting apparatus that can accommodate the broader demands of, for example, an enzyme immune measurement system in an economical and highly efficient manner.

SUMMARY OF THE INVENTION

It is an object of the present invention to provide an improved chemical luminescence-detecting apparatus capable of positively detecting a wide range of intensities of chemical luminescence generated in a photometric cell.

The purposes of the present invention are addressed by providing a chemical luminescence-detecting apparatus having a plurality of optical detectors of different sensitivities positioned in the vicinity of the sample photometric cell. The relationships between a ratio of the outputs of each of the optical detectors, based on the intensity of luminescence, are previously ascertained and stored. The detecting apparatus is capable of responding when it is determined that any of the optical detectors having a high sensitivity has become saturated so that its output is invalid. Under these conditions, the outputs of relatively low sensitivity optical detectors can be utilized by multiplying their outputs by a factor that has been stored and determined by a ratio of outputs from the appropriate optical detectors. Thus, a conversion value corresponding to the outputs from a high sensitivity optical detector to a low sensitivity optical detector may be obtained, and this conversion factor can be utilized with the low sensitivity optical detector output, to provide an equivalent value of the high sensitivity optical detector beyond its limited range.

As can be readily appreciated, a chemical luminescence-detecting apparatus having multiple optical detectors that are different in sensitivity enable an increased range of sensitivity for the entire detecting apparatus.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved chemical luminescence-detecting apparatus that can reliably produce measurements in an economical manner over a wide range of chemical luminescence.

Figure 1:
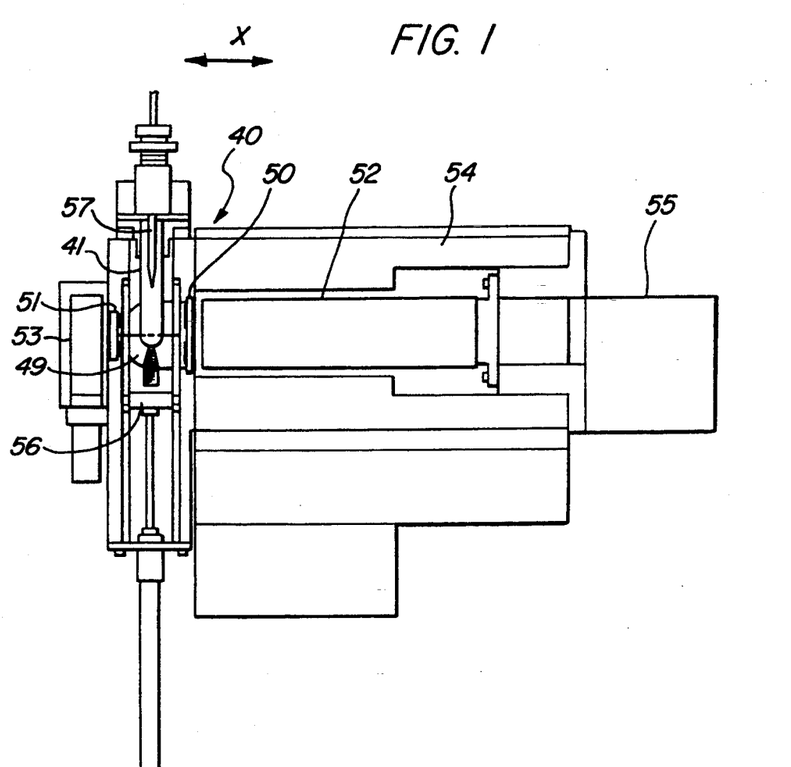
FIG. 1 is a schematic sectional view showing one example of a chemical luminescence-detecting apparatus according to the present invention.
Figure 3:
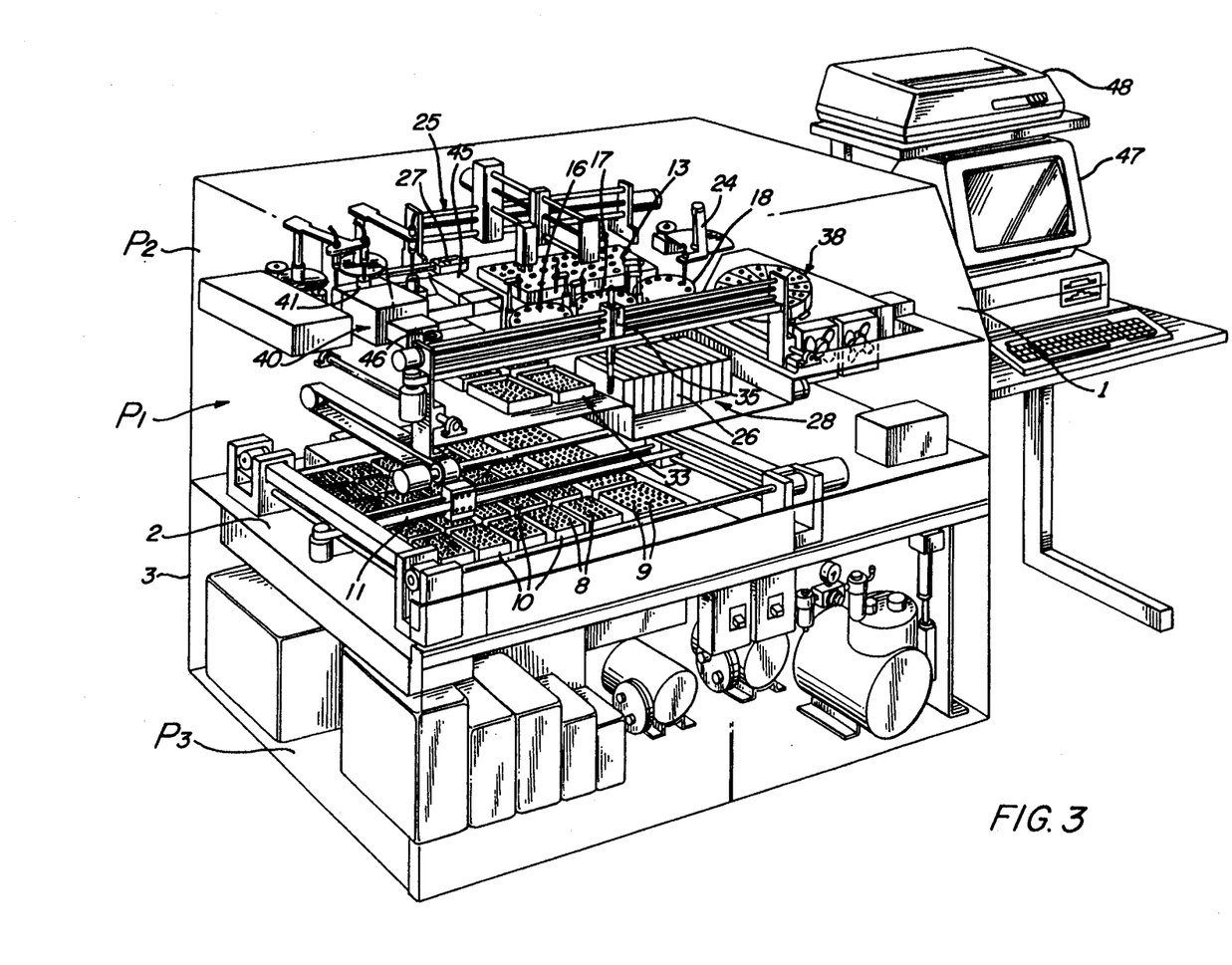
FIG. 3 is a perspective schematic view disclosing an enzyme immuno assay system with a chemical luminescence-detecting apparatus incorporated.
Figure 4:
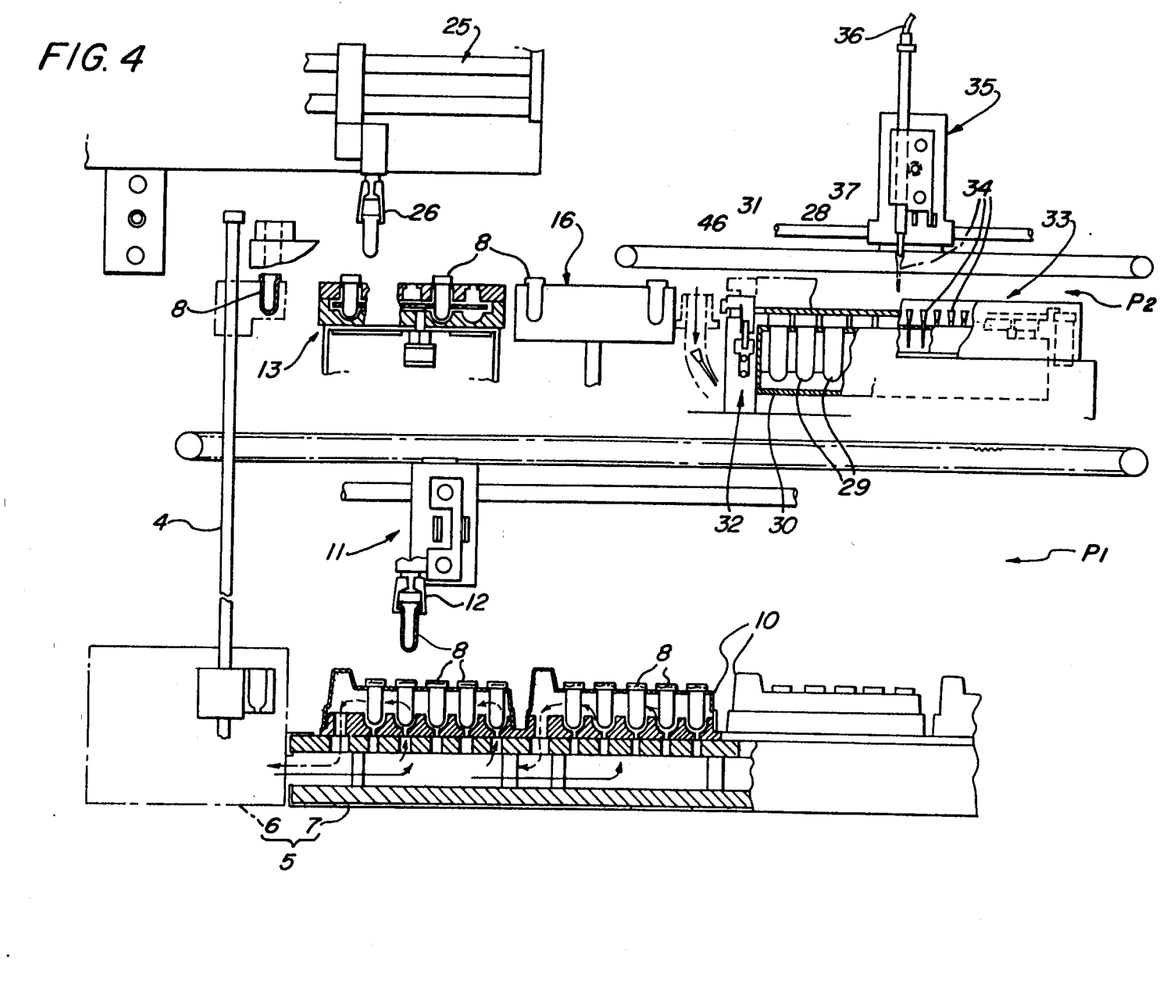
FIG. 4 is a schematic partial view of the enzyme immuno assay system.
Figure 5:
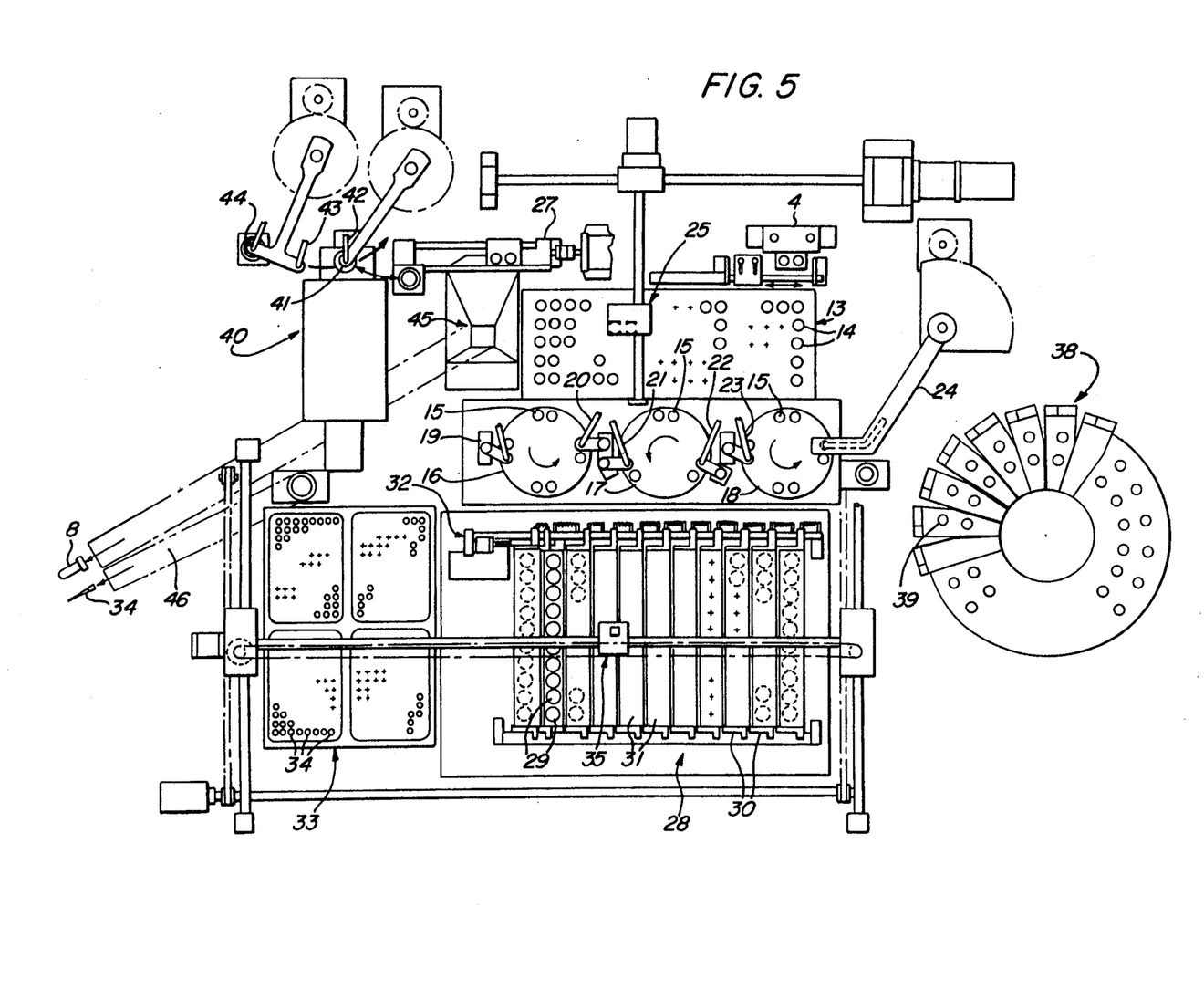
FIG. 5 is a schematic plan view showing various component parts of the chemical luminescence-detecting apparatus.

FIG. 1 illustrates a first preferred chemical luminescence-detecting apparatus according to the present invention utilizing a pair of photomultiplier optical detectors. FIGS. 3 to 5 depict the general construction of an enzyme immuno assay system in which the preferred chemical luminescence-detecting apparatus of FIG. 1 can be employed.

As shown in FIG. 3, the enzyme immuno assay system includes partition plates 1, 2 that generally divide an inner space of an apparatus case 3 into three separate spaces: a central space $P_1$, an upper space $P_2$, and a lower space $P_3$. The central space $P_1$ is principally comprised of a test tube cooling device 5 that includes a suction exhaust portion 6 connected between a cooling case 7 and a cooler (not shown) provided in the lower space $P_3$. A plurality of test tube support cases 10, having open aperture bottoms, are detachably placed on an upper surface of the cooling case 7. The cooling case 7 can be freely withdrawn from the front side of the apparatus case 3. The tube supporting case 10 is positioned on an upper surface of the cooling case 7 to complete a cooling duct, as shown in FIG. 4. Reference numeral 8 designates "antibody test tubes" having an antibody reactant material or additive immobilized on an inside surface thereof and sealed to preserve the reactant with a cover of aluminum foil. A series of dilution test tubes 9 are also shown in FIG. 3.

As shown in both FIGS. 3 and 4, a first horizontal tube conveying mechanism 11 having a test tube chuck or gripper 12 is provided for conveying the antibody test tubes 8 (and the dilution test tubes 9 if needed) to a lower end of a test tube elevator 4. The conveying mechanism 11 is horizontally movable in two dimensions and has an elevatable vessel chuck 12. The test tube elevator 4 can be moved from a lower end in the central space $P_1$ to an upper end in the upper space $P_2$, and has a holder for supporting a test tube.

The upper space $P_2$ includes a constant temperature shaker 13 having a plurality of apertures 14 for receiving test tubes and first to third rotors 16, 17, 18 having apertures 15. The apertures 14, 15 are sized for insertion of the antibody test tubes 8. As shown in FIG. 5, a washer 19 and a diluent dispenser 20 are arranged above the first rotor 16; a washer 21 and a substrate solution dispenser 22 are arranged above the second rotor 17; and a washer 23 and an enzyme conjugated antibody reagent dispenser 24 are arranged above the third rotor 18. The rotors 16, 17, 18 may be rotated in an appointed direction as shown, for example, by the arrows in FIG. 5.

A second horizontal tube conveying mechanism 25 having a test tube chuck or holder 26 is movable in three dimensions, and is provided in the upper space $P_2$ for conveying the antibody test tubes between any one of the test tube elevator 4, the constant temperature shaker 13, the first to third rotors 16, 17, 18, and a sample portion 27.

The upper space $P_2$ further comprises a sample tube storage portion 28 including a plurality of sample tube cases 30, each sample tube case 30 housing a plurality of individual sample tubes 29. A plurality of covers 30 and a cover member closing mechanism 32 are provided to selectively close the upper openings of the sample tube housing cases 31. As explained further herein, a sample, such as blood serum, may be poured in the sample tubes 29 in the left and right direction, as suggested in FIGS. 4 and 5. A cover member 31 can close over the sample tube 29 as a result of activation of closing mechanism 32.

Also provided is a supply area 33 of pipette tips 34, located adjacent to the sample tube housing portion 28. As shown in FIGS. 4 and 5, a sample dispensing mechanism 35, including a freely elevatable probe 37 connected to a suction exhaust pipe 36, is movable in two horizontal directions over any one of the pipette supply area 33, the sample tube housing portion 28, and the first rotor 16. A pipette tip 34 may be placed on a lower end of the probe 37 through a descending movement of the probe 37 within the pipette stock area 33. A sample from one of the sample tubes 29 may then be sucked into the pipette tip 34 while the sample dispensing mechanism 35 is above the sample tube housing portion 28, and then the sample may be discharged in an antibody test tube 8 held in the first rotor 16 after locating the sample dispensing mechanism 35 above the first rotor 16.

The upper space $P_1$ is further comprised of a reagent bottle supplier 38 having a plurality of reagent bottles 39 containing the enzyme conjugated antibody reagent.

A photometric portion 40 provided with a glass tube photometric cell 41 is provided adjacent to the sample portion 27. A reactant dispenser 42 is provided for transferring a reactant in the antibody test tube 8 located in the sample portion 27 into the photometric cell 41. A reagent dispenser 43 is provided for pouring a luminescent reagent (for example, luminol solution) into the photometric cell 41, and a washer 44 is provided for cleansing the photometric cell 41. First and second chutes 45, 46 are provided for respectively transporting a previously-used antibody test tube 8 and pipette tip 34 to the outside.

A testing system of the above-described construction may be used to implement an enzyme immuno assay with, for example, a two-step sandwich method, as follows:

The antibody test tube 8 containing the antibody to be measured is taken from the central space $P_1$ to an aperture 15 of the first rotor 16 via the first horizontal test tube conveying mechanism 11, the test tube elevator 4, and the second horizontal test tube conveying mechanism 25. The aluminum foil sealing the upper opening of the antibody test tube 8 is broken in the process of transporting the antibody test tube 8. The antibody test tube 8 is deposited in an aperture 15 of the first rotor 16.

The probe 37 is then provided with a new pipette tip 34 at a lower end thereof. The probe 37 and the pipette tip 34 are positioned over a sample tube 29 so that a sample contained therein may be sucked into the pipette tip 34 and then poured into the antibody test tube 8 located in the first rotor 16. After the sample has been poured into the antibody test tube 8, the pipette tip is discarded via chute 46.

The first rotor 16 is rotated a predetermined amount, and then a diluent is poured into the antibody test tube 8 from the diluent dispenser 20. The antibody test tube is then moved into the constant temperature shaker 13 and shook for an appointed time at body temperature to carry out a first immuno reaction.

The antibody test tube is then moved to the second rotor 17 to be washed and then subjected to a so-called B/F separation. An appointed amount of substrate solution corresponding to the item to be measured is then poured into the antibody test tube 8 from the dispenser 22. The antibody test tube 8 is then moved back to the constant temperature shaker 13 to carry out a second immuno reaction.

The antibody test tube is now moved to the third rotor 18 to be washed and to then have an appointed quantity of enzyme conjugated antibody reagent poured therein from dispenser 24. The antibody test tube is returned to the constant temperature shaker 13 for a third time to carry out an enzyme reaction, during which reaction hydrogen peroxide is generated in a quantity corresponding to the quantity of the substance to be measured by this reaction.

After the enzyme reaction, the antibody test tube 8 is conveyed with the second horizontal test tube conveying mechanism 25 to the sample portion 27. The reaction solution containing hydrogen peroxide in the antibody test tube 8 is then added to the photometric cell, into which the luminescent reagent was previously poured, to carry out a luminescent reaction. The antibody test tube 8 is then discarded via chute 45.

During the above-described luminescent reaction, a luminescent quantity is electrically measured by a sensor and its output signal is processed with the assistance of a computer. The concentration of the luminescent substance is then displayed as an analytical result on a monitor 47 or a printer 48.

The photometric portion of the above-described enzyme immuno assay system is shown in more detail in FIG. 1. As shown, the photometric cell 41 is held by a cell holder 49 having an integrated spherical shape. An interference filter 50 and a high sensitivity photomultiplier tube ("HPMT") 52 is disposed on one side of the photometric cell, and an interference filter 51 and a low sensitivity photomultiplier tube ("LPMT") 53 is disposed on the other side. The HPMT 52 and the LPMT 53 are disposed in a straight line, as seen from the direction of an arrow X. The HPMT 52 includes a housing 54 provided with a cooler (not shown) for reducing the dark current inherent in a photomultiplier tube. Also provided are an amplifier 55 for the HPMT 52, a shutter 56, and a reactant pouring nozzle 57.

Because the sensitivity of the HPMT 52 is vastly different from that of the LPMT 53, an output signal of the HPMT 52 is at a vastly different level than an output signal from the LPMT 53. Thus, a concentration signal may only be obtained by separately converting the respective output signals into a signal quantity, as shown by the construction of FIG. 2.

Figure 2:
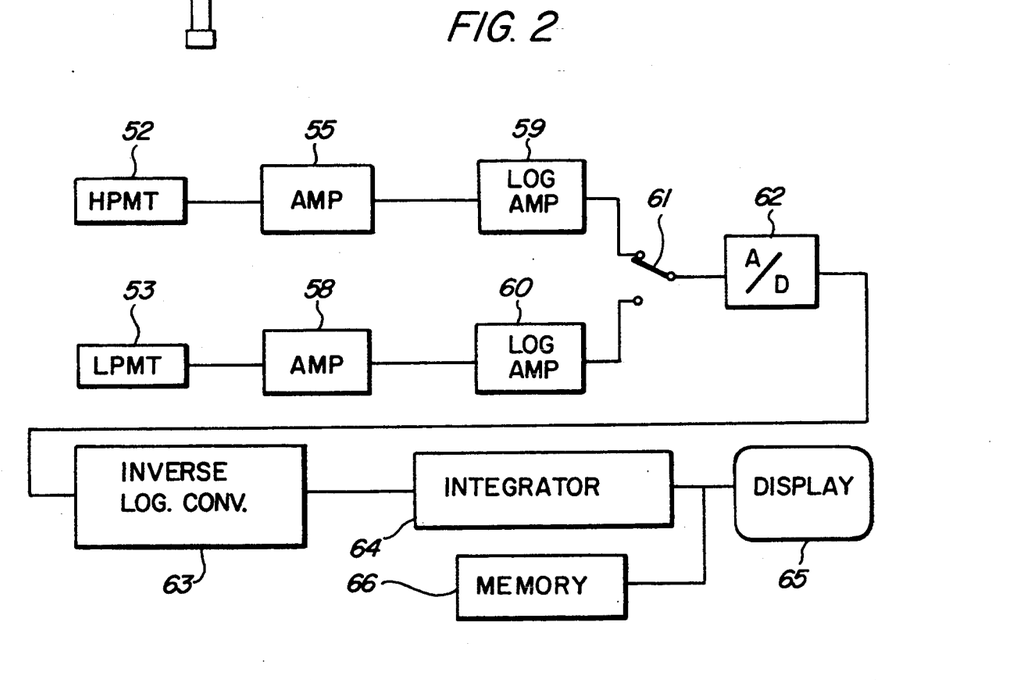
FIG. 2 is a schematic block diagram disclosing a schematic of a circuit for the chemical luminescence-detecting apparatus of the present invention.

FIG. 2 schematically depicts the connections between the HPMT 52 and the LPMT 53. Included are amplifiers 55, 58, log amplifiers 59, 60, a changeover switch 61, an A/D converter 62, an inverse log converter 63, an integrator 64, a display 65, and a memory 66.

The log amplifiers 59, 60 and the inverse log converter 63 are not always required, depending upon the measuring range and the range of the A/D converter 62. It is to be further understood that the position of the changeover switch 61 is not limited to that shown. For example, if two A/D converters were used, one each for the HPMT 52 and the LPMT 53, then the switch 61 may be disposed on the output sides of the two A/D converters.

In operation, the changeover switch 61 is set such that the output of the HPMT 52 is provided to the A/D converter 62. The changeover switch 61 is an analog switch for alternately putting the output signal from the HPMT 52 and the output signal from the LPMT 53 in the A/D converter 62 every 50 msec to put the data in two.

In this preferred embodiment, the radiant life is usually about 10 seconds and, as described above, the output from the detector is alternately taken out one by one every 50 msec so that, finally, the output from the respective detectors is divided into 200 pieces to be put in the computer. (The integral value of the respective outputs becomes the datum adopted in the operation of concentration.) The signal from the HPMT 52 and the signal from the LPMT 53 are digitized by the A/D converter 62 and stored in the computer. At this time, the signal from the HPMT 52 is preferentially adopted as the datum for the operation of concentration and, in the case where the signal from the HPMT 52 exceeds the regulation current, the signal from the LPMT 53 is adopted. The output of the LPMT 53 is then multiplied by a factor determined by a ratio of the HPMT 52 output to the LPMT 53 output that was determined in previously-determined luminescent intensities and stored for this purpose. As can be appreciated, a comparator can monitor the output signal of the HPMT by comparing it with a predetermined signal level which defines an unreliable saturation output from the HPMT. The comparator can then activate the changeover switch 61 in an automatic manner.

Figures 10, 12:
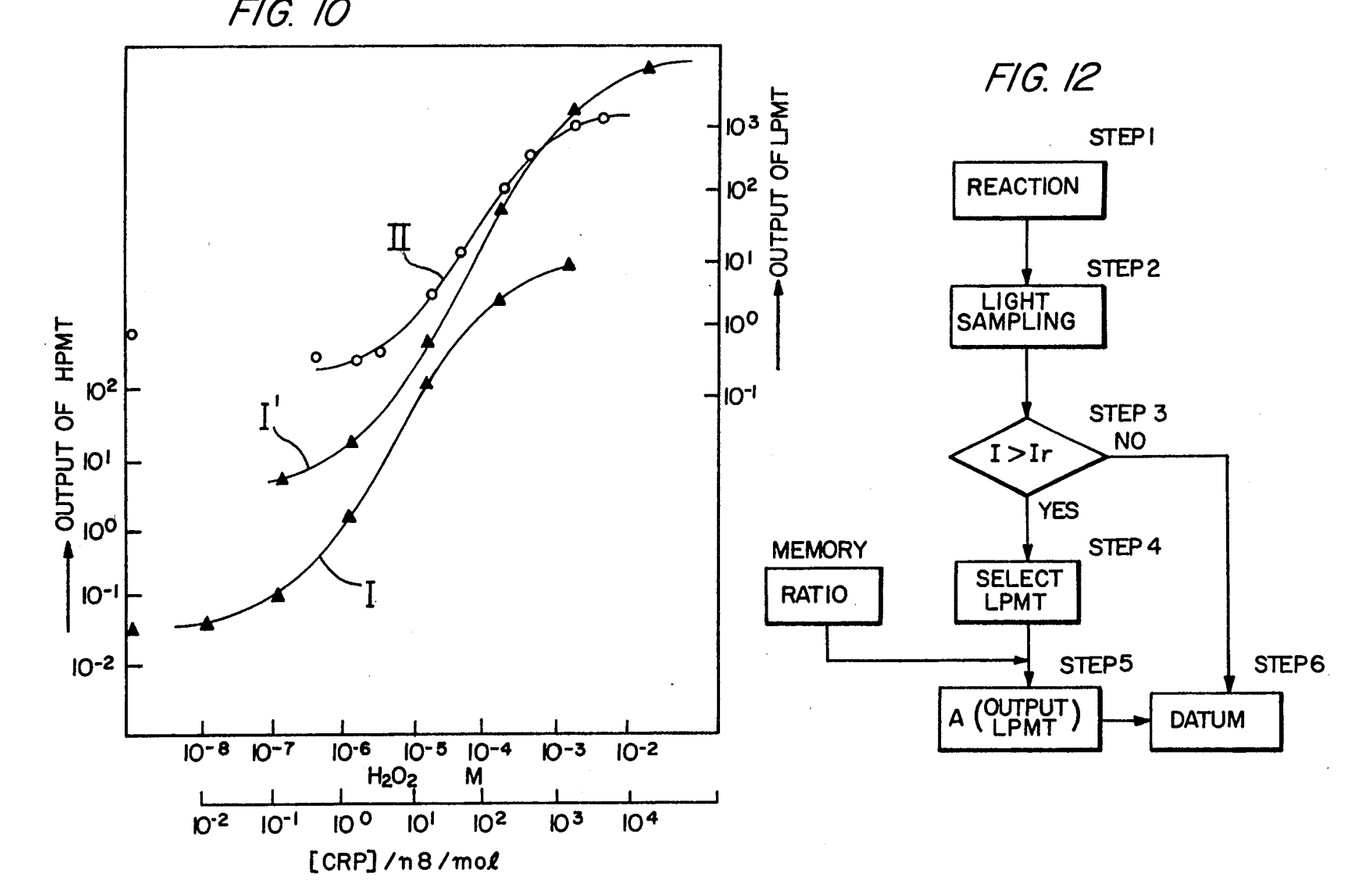
FIG. 10 is a diagram showing comparisons of the output of an HPMT and an LPMT.
FIG. 12 is a schematic flow diagram of a control procedure used in selecting an output from one of the HPMT and the LPMT.

FIG. 12 is a schematic flow diagram of the control procedure used in selecting the HPMT 52 or the LPMT 53. At Step 1, a chemical luminescent reaction is carried out as described above. At Step 2, the luminescent data is sampled with both of the optical detectors (HPMT 52 and LPMT 53). At Step 3, it is determined whether or not the output of the HPMT 52 exceeds the regulation current. If the HPMT 52 output does not exceed the regulation current then, at Step 6, its output is adopted as the datum to derive the concentration. If the output of the HPMT 52 does exceed the regulation current then, at Step 4, the output from the LPMT 53 is adopted instead. At Step 5, the output from the LPMT 53 is multiplied by a ratio "A," stored in the memory 66 and described below, which product is then adopted as the datum to derive the concentration.

Figure 9:
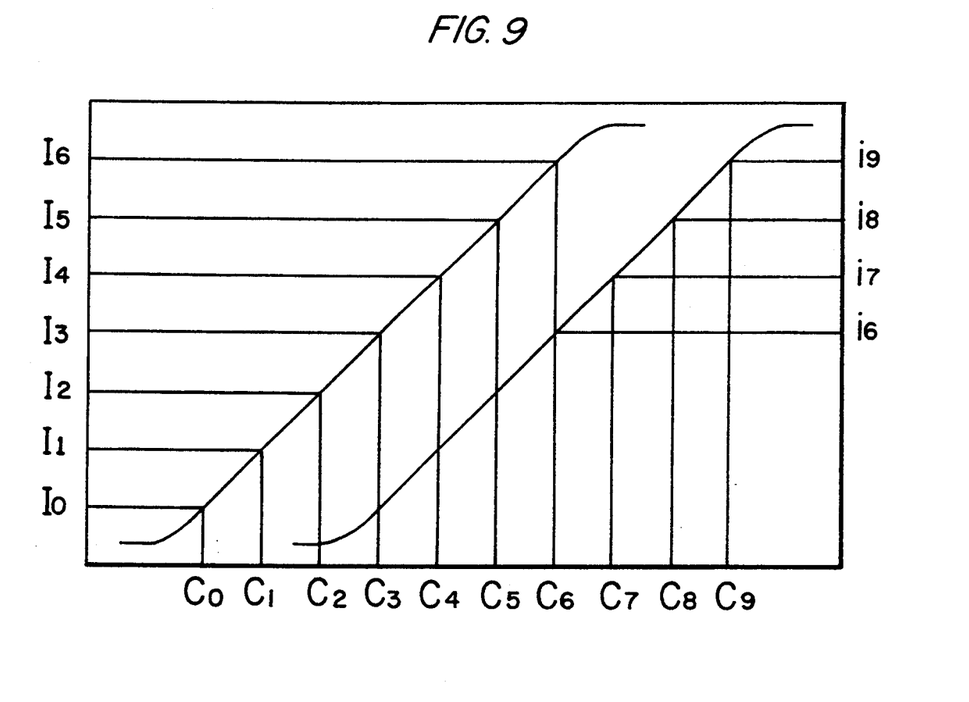
FIG. 9 is a graph showing the relationship between the output from a high sensitivity photomultiplier tube (HPMT) and the output from a low sensitivity photomultiplier tube (LPMT) for different concentrations of a luminous substance (C)

The graph of FIG. 9 depicts the relationship between the output of the HPMT 52 and the output of the LPMT 53 as a function of a concentration of a luminescent substance $C_0$ to $C_9$. The designations $I_0$ to $I_6$ on the left side of the ordinate designate the output of the HPMT 52 for concentrations $C_0$ to $C_6$, and the designations $i_6$ to $i_9$ on the right side of the ordinate designate the output from the LPMT 53 for concentrations $C_6$ to $C_9$. Accordingly, the ratio ("A") of the HPMT 52 output to the LPMT 53 output based on the luminescent intensities $C_0$ to $C_9$ can be determined.

For example, provided that the HPMT 52 output is $I_r$ and the LPMT 53 output is $i_r$, the ratio A can be determined as $I_r/i_r$. Thus, it may be detected by means of the LPMT 53 that the output from the HPMT 52 has saturated, and then an output i from the LPMT 53 may be converted, with the expression $I = i \times A$, into an output I equivalent to that from the HPMT 52 were it not saturated.

Referring to FIG. 10, a graph is disclosed showing the results achieved by measuring samples in the photometric portion 40 of the first embodiment of the present invention.

Referring to FIG. 10, an axis of abscissa designates a concentration of $H_2O_2$ and a concentration of CRP (C reactive proteins), an axis of ordinate on the left side designates the output from the HPMT 52, while an axis of ordinate on the right side designates the output from the LPMT 53. Curve I shows a measurement of a change of concentration of $H_2O_2$ by the HPMT 52, while a curve I' shows a measurement of a change of the concentration of $H_2O_2$ by the LPMT 53. When a detecting range of the HPMT 52, converted into the concentration of $H_2O_2$, is $10^{-8}$ to $10^{-4}$M, and a detecting range of the LPMT 53, converted into the concentration of $H_2O_2$, is $10^{-6}$ to $10^{-2}$M, as shown by the curves I, I', then the detecting range of the entire apparatus is $10^{-8}$ to $10^{-2}$M. In addition, a curve II is a calibration curve of CRP (C reactive proteins) obtained by the enzyme immuno assay, and expresses the output from the HPMT 52 and the output from the LPMT 53 in the form of one continuous calibration curve following the above-described method.

Figures 6, 7, 8:
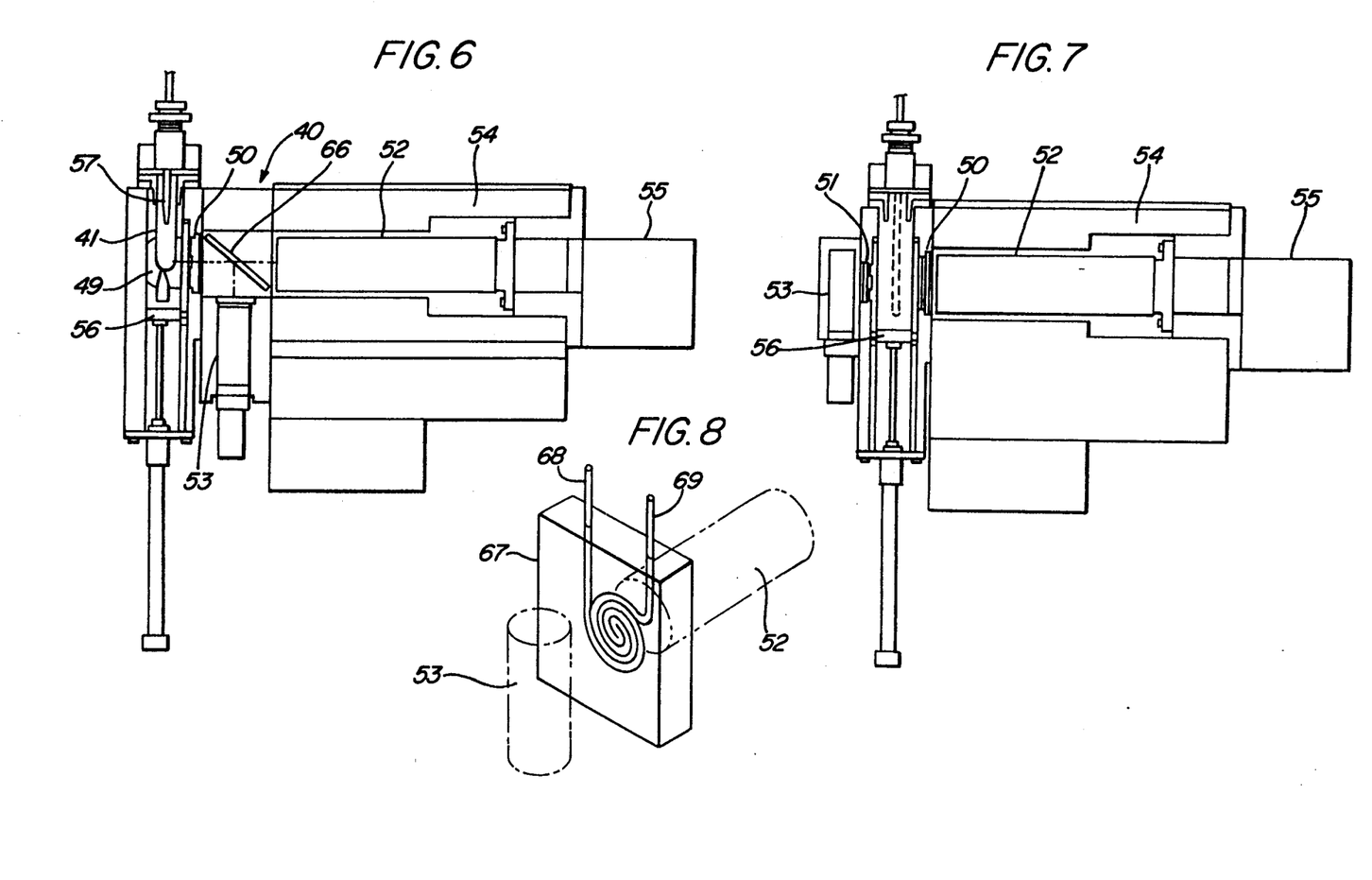
FIG. 6 is a partial sectional elevated view showing a chemical luminescence-detecting apparatus according to a second embodiment of the present invention.
FIG. 7 is a partial sectional elevated view showing a chemical luminescence-detecting apparatus of a third embodiment of the present invention.
FIG. 8 is a perspective view showing components of the apparatus shown in FIG. 7.

Although the HPMT 52 and the LPMT 53 are arranged along a straight line with the photometric cell 41 positioned therebetween in the above-described preferred embodiment, the HPMT 52 and the LPMT 53 may be positioned by the use of an optical splitter 66 (for example, a half mirror, silica plate, glass plate, and the like) so that the HPMT 52 may be arranged at 90 degrees relatively to the LPMT 53, as shown in the embodiment of FIG. 6. In such a case, since a luminescent axis will be common to both the HPMT 52 and the LPMT 53, an advantage occurs in that it is unnecessary to take any optical positional condition into consideration that could affect the amount of light received by each sensor.

The present invention can be applied to not only the above-described so-called batch-type measuring method, but also a so-called flow through-type measuring method using a spiral flow through-type photometric cell 67, as shown in FIGS. 7 and 8. Referring to FIG. 8, reference numerals 68, 69 designate an introducing portion and a discharging portion of a reactant solution and the like, respectively.

A silicon photodiode and the like can also be used as the optical detector in addition to the above-described photomultiplier tube. The present invention can be applied to not only the photometric portion of the above-described enzyme immuno assay system, but also photometric portions of other analyzers and the like.

As described above, a plurality of optical detectors that are different in sensitivity are provided in the vicinity of the photometric cell, so that the measuring range of sensitivity of the whole detecting apparatus is the sum total of the range of sensitivities of each of the optical detectors. Thus, a wider range of measurement can be realized in comparison with the conventional detectors where merely a single optical detector is used. The ratio of outputs from the individual optical detectors, based on the intensity of luminescence, is previously determined and stored, so that it is possible to multiply the output of a low sensitivity optical detector by a factor determined by the ratio so that a conversion value corresponding to an output from a high sensitivity optical detector may be obtained when the output from the high sensitivity optical detector is erroneous because of saturation. As a result, a highly accurate measurement can be achieved ranging from a low sensitivity zone to a high sensitivity zone.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A chemical luminescence-detecting apparatus in which an intensity of chemical luminescence generated can be measured, comprising:

means for movably supporting test tubes;
means for introducing a sample into a test tube;
means for causing an immuno reaction to be carried out with the sample in the test tube;
means for causing an immuno reaction to be carried out with the sample in the test tube;
means for causing a luminescent reaction to be carried out that is representative of the immuno reaction in the test tube;
a cell holder having an integrated spherical shape with a central cavity for supporting the test tube;
a first and second interference filter;
a first and second optical detector operatively positioned adjacent the test tube with the luminescent reaction, and behind the respective first and second interference filters; one optical detector having a relatively low sensitivity to luminescence, and the other having a higher sensitivity, the effective ranges of the respective detectors overlapping, and the higher sensitivity detector range having a saturation level before the lower sensitivity detector, the higher sensitivity optical detector and the low sensitivity optical detector are arranged on opposite sides of the central cavity;

means for determining when the higher sensitivity detector becomes saturated;

means for processing output signals from the detectors to provide an indication of the intensity of luminescence, and means for switching the output signal being processed from the higher sensitivity detector to the low sensitivity detector when the means for determining indicates saturation of the higher sensitivity detector.

2. A chemical luminescence-detecting apparatus in which an intensity of chemical luminescence generated can be measured, comprising:

means for movably supporting test tubes;

means for introducing a sample into a test tube, including a pipette tip for contacting the sample and withdrawing a portion of the sample in the pipette tip and subsequently discharging the sample into the test tube;

means for causing an immuno reaction to be carried out with the sample in the test tube;

a photometric cell;

means for introducing the immuno reacting sample into the photometric cell;

means for causing a luminescent reaction to be carried out that is representative of the immuno reaction in the photometric cell;

a cell holder having an integrated spherical shape with a central cavity for supporting the photometric cell;

means for automatically discharging the used pipette tip and test tube from the apparatus;

a pair of interference filters;

at least a pair of optical detectors operatively positioned to directly receive the light from the luminescent reaction after passing through the interference filters, one optical detector having a relatively low sensitivity to luminescence, and the other having a higher sensitivity, the effective ranges of the respective detectors overlapping, and the higher sensitivity detector range having a saturation level before the lower sensitivity detector, the higher sensitivity optical detector and the low sensitivity optical detector are arranged on opposite sides of the central cavity;

means for determining when the higher sensitivity detector becomes saturated;

means for processing output signals from the detectors to provide an indication of the intensity of luminescence, and means for switching the output signal being processed from the higher sensitivity detector to the low sensitivity detector when the means for determining indicates saturation of the higher sensitivity detector.

3. A chemical luminescence-detecting apparatus as set forth in claim 2, including a switch member to sequentially sample in series the output of the low sensitivity detector and the high sensitivity detector.

4. A chemical luminescence-detecting apparatus as set forth in claim 3, further including an analog-to-digital converter for converting the output to a digital format.

5. A chemical luminescence-detecting apparatus as set forth in claim 4, further including a logarithm amplifier, inverse logarithm converter, and integrator circuit for processing the output of an optical detector.

6. A chemical luminescence-detecting apparatus in which an intensity of chemical luminescence generated can be measured, comprising;

means for movably supporting an antibody containing test tubes;

means for introducing a sample into an antibody containing test;

means for causing an immuno reaction to be carried out with the sample in the test tube;

a photometric cell;

means for causing a luminescent reaction to be carried out that is representative of the immuno reaction in the photometric cell;

a spherical-shaped holder having a central cavity for supporting the photometric cell;

at least a pair of optical detectors operatively positioned adjacent the holder supporting the photometric cell with the luminescent reaction;

a first interference filter positioned between the holder and one optical detector having a relatively low sensitivity to luminescence;

a second interference filter positioned between the holder and the other optical detector having a higher sensitivity to luminescence; the effective ranges of the respective detectors overlapping, and the higher sensitivity detector range having a saturation level before the lower sensitivity detector, the first interference filter and one optical detector are positioned on one side of the central cavity and the second interference filter and the other optical detector are positioned on the opposite side of the central cavity;

means for determining when the higher sensitivity detector becomes saturated;

means for processing output signals from the detectors to provide an indication of the intensity of luminescence, and means for switching the output signal being processed from the higher sensitivity detector to the low sensitivity detector when the means for determining indicates saturation of the higher sensitivity detector.

7. A chemical luminescence-detecting apparatus as set forth in claim 6, wherein the processing means further includes means for storing a conversion value to compensate an output of the low sensitivity detector so that it provides a complementary reading beyond a normal range of outputs of the high sensitivity detector.

* * * * *